(12) United States Patent
Stein et al.

(10) Patent No.: US 8,217,357 B2
(45) Date of Patent: Jul. 10, 2012

(54) INTEGRATED BREAST X-RAY AND MOLECULAR IMAGING SYSTEM

(75) Inventors: Jay Stein, Boston, MA (US); Baorui Ren, Andover, MA (US); Andrew P. Smith, Lexington, MA (US); Kenneth F. Brooks, Knoxville, TN (US); Jing Zhenxue, Chadds Ford, PA (US); Ian Shaw, Yorktown Heights, NY (US); Ken DeFreitas, Patterson, NY (US)

(73) Assignee: Hologic, Inc., Marlborough, MA (US)

( * ) Notice: Subject to any disclaimer, the term of this patent is extended or adjusted under 35 U.S.C. 154(b) by 459 days.

(21) Appl. No.: 12/422,806

(22) Filed: Apr. 13, 2009

(65) Prior Publication Data

US 2010/0260316 A1   Oct. 14, 2010

(51) Int. Cl.
*G01N 23/02* (2006.01)
(52) U.S. Cl. ............... 250/366; 250/370.09; 378/63
(58) Field of Classification Search ............. 250/363.02, 250/363.03, 363.04, 363.1, 366, 370.08, 250/370.09; 378/62, 63
See application file for complete search history.

(56) References Cited

U.S. PATENT DOCUMENTS

| | | | |
|---|---|---|---|
| 6,389,098 B1 | 5/2002 | Keppel | |
| 6,928,142 B2 * | 8/2005 | Shao et al. | 378/63 |
| 2003/0194050 A1 | 10/2003 | Eberhard et al. | |
| 2005/0069086 A1 * | 3/2005 | Deych et al. | 378/112 |
| 2007/0223651 A1 | 9/2007 | Wagenaar | |
| 2008/0061242 A1 | 3/2008 | Vija | |

* cited by examiner

*Primary Examiner* — Mark R Gaworecki
(74) *Attorney, Agent, or Firm* — Hologic, Inc.

(57) ABSTRACT

An integrated tomosynthesis/molecular breast imaging device having improved sensitivity includes tomosynthesis imaging components and molecular breast imaging components. The imaging components may be used individually or in combination to provide a system with improved sensitivity and specificity. Molecular imaging components may be smoothly advanced or withdrawn depending upon the desired imaging mode. The system supports both PET and SPECT imaging and enables SPECT collimation to be modified in accordance with image capture requirements.

27 Claims, 18 Drawing Sheets single photon positron

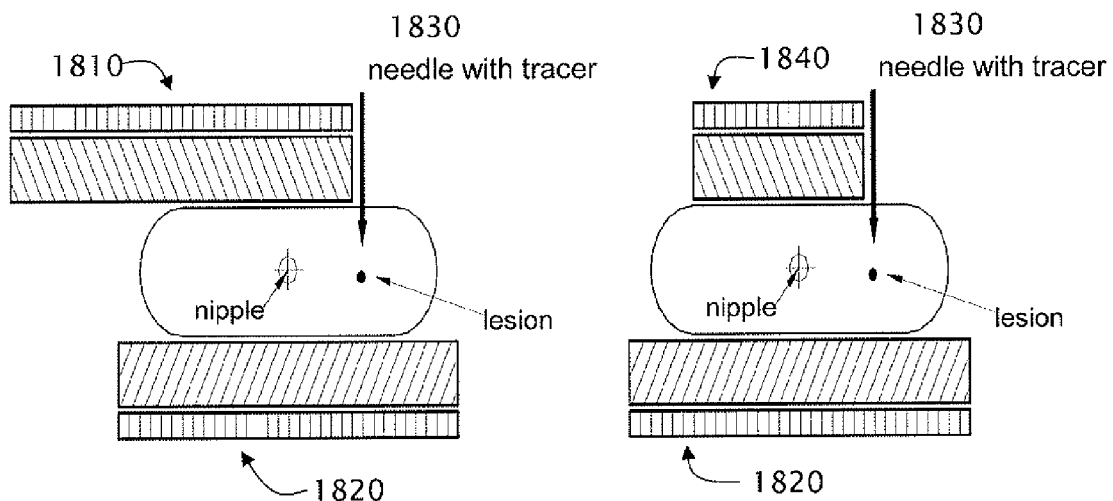
Figure 18A
Figure 18B
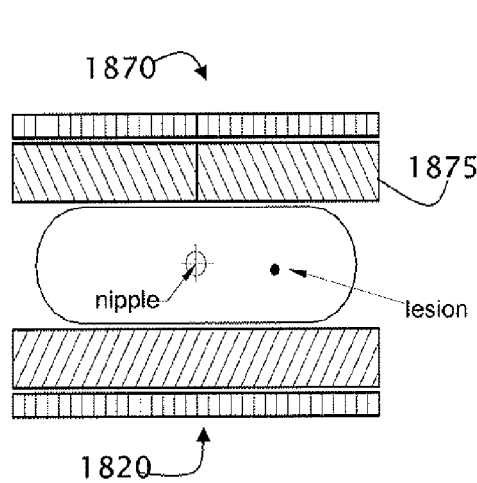
Figure 18C
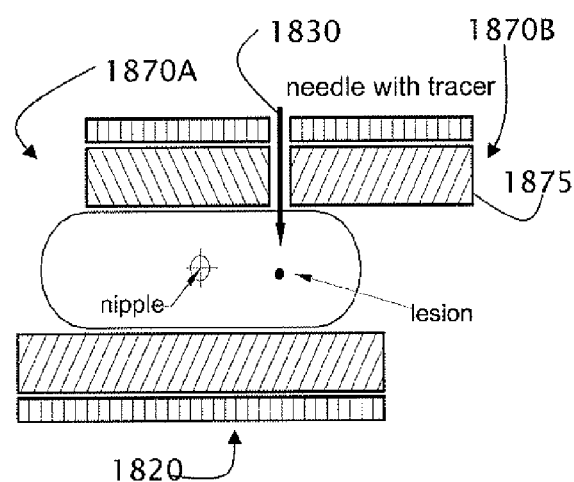
Figure 18D

INTEGRATED BREAST X-RAY AND MOLECULAR IMAGING SYSTEM

FIELD OF THE INVENTION

This invention relates generally to the field of breast imaging and more particularly to a system and process for breast imaging which integrates multiple imaging modalities such as tomosynthesis imaging and molecular breast imaging into a single imaging device.

BACKGROUND OF THE INVENTION

The quality of a breast cancer imaging technique is frequently evaluated in terms of its sensitivity and specificity. Sensitivity is the ability of the imaging technology to detect a cancerous lesion. Specificity is the ability of the imaging technology to ignore objects in images which merely appear similar to lesions. It is thus desirable to use a breast cancer imaging technology that is both sensitive (to ensure that cancerous lesions are not missed) and specific (to reduce the number of medical procedures when no cancer is present).

Mammography is currently the most frequently utilized FDA approved method for breast cancer screening. However, mammograms suffer in both the area of sensitivity and specificity. During a mammogram, x-rays are directed at compressed breast tissue to generate one or more images (mammograms) of the breast for review. However, because mammograms are two dimensional representations of a three dimensional structure, the sensitivity of a mammogram is compromised due to overlapping structures in the compressed breast. In addition, the similarity of x-ray attenuation characteristics between breast tissue and cancerous tissue increases the difficulty of differentiating cancerous lesions from breast tissue, particularly when imaging dense breast tissue.

Efforts to improve the sensitivity and specificity of breast x-rays have included the development of breast tomosynthesis systems. Breast tomosynthesis is a three-dimensional imaging technology that involves acquiring images of a stationary compressed breast at multiple angles during a short scan. The individual images are then reconstructed into a series of thin, high-resolution slices that can be displayed individually or in a dynamic ciné mode.

Reconstructed tomosynthesis slices reduce or eliminate the problems caused by tissue overlap and structure noise in single slice two-dimensional mammography imaging. Digital breast tomosynthesis also offers the possibility of reduced breast compression, improved diagnostic and screening accuracy, fewer recalls, and 3D lesion localization. Examples of breast tomosynthesis systems are described in U.S. Pat. application Nos. 7,245,694 and 7,123,684, commonly owned by the Assignee of this application. While breast tomosynthesis methods greatly improve the sensitivity of x-ray cancer screening, specificity issues associated with dense breasts remain an issue.

Perhaps the most sensitive breast imaging modality is Molecular Resonance Imaging (MRI). However the sensitivity of the MRI modality negatively affects its specificity. In addition, the cost of the MRI devices limits their general deployment. Molecular Breast Imaging (MBI) has advanced considerably in recent years as more clinical data has become available. The clinical advantages of MBI include sensitivity similar to that of MRI modalities but with a much better specificity and at a much lower cost

SUMMARY OF THE INVENTION

According to one aspect of the invention it is realized that breast cancer diagnosis may be improved via the introduction of an integrated multi-modal breast imaging system which combines tomosynthesis imaging capability with molecular imaging capability in a single, integrated breast imaging device. Tomosynthesis capability is provided using breast X-ray components capable of performing mammography, tomosynthesis and stereotactic imaging for routing breast cancer screening and diagnosis. The x-ray components generate two-dimensional and three-dimensional anatomical images based on the absorption of x-rays by the breast.

The integrated device also provides molecular imaging capability via molecular imaging components capable of imaging a breast using methods such as single photon planar imaging, Positron Emission Tomography (PET), and Single Photon Emission Computed Tomography (SPECT). Molecular imaging may be used on its own or in conjunction with x-ray imaging. Molecular breast imaging generates a physiological image of the breast based on the absorption and decay of radioisotopes that have been injected into the breast.

The present invention fuses tomosynthesis imaging capability and molecular imaging capabilities into a single breast imaging device. Integrating the different imaging modalities into a single imaging device may increase the speed and accuracy of diagnosis by enabling the radiologist to tune the diagnostic workflow according to the particular needs of each patient. For example the radiologist may choose to use one modality over another depending upon a known anatomical structure (i.e., density) of the patient's breast. Or the radiologist may use the two diagnostic imaging methods in sequence to obtain additional information as needed. For example, if a routine mammogram such as that shown in FIG. 1A, obtained using the x-ray components, suggests the presence of a lesion 10, the radiologist may opt to obtain a molecular image of the patient's breast during the patient's visit. The molecular image verifies the presence of lesion 10, while also highlighting additional calcifications 12, 14, which may have been missed in the x-ray image. The present invention enables tomosynthesis images and molecular images to be viewed together on a single display, either side by side (for example providing both FIGS. 1A and 1B on a display), overlaid, in cine mode, etc. The ability to obtain the molecular image with the same equipment during a single office visit facilitates registration of the images, allows comparison of the anatomical and physiological information of the breast at a slice granularity, allows comparison of CAD results of the images, increases the speed and accuracy of the diagnosis and thereby reduces unnecessary biopsies and concomitant patient anxiety.

According to one aspect of the invention, a breast imaging device includes tomosynthesis imaging components for obtaining tomosynthesis images of an anatomical structure of a breast and molecular imaging components for obtaining molecular breast images of a physiological structure of the breast.

According to a further aspect of the invention, a method of imaging a breast in an integrated tomosynthesis/molecular breast imaging (T/MBI) device includes the steps of compressing the breast, performing a tomosynthesis scan of the breast, obtaining a molecular image of the breast and decompressing the breast

BRIEF DESCRIPTION OF THE FIGURES

FIGS. 18A-18D illustrate exemplary embodiments of dual head molecular breast imaging cameras for needle biopsies;

DETAILED DESCRIPTION

Figure 1A:
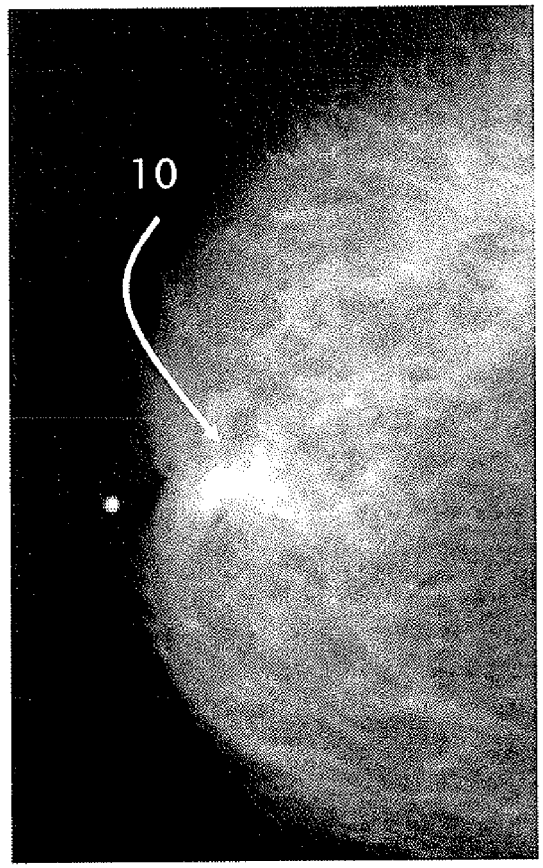
FIGS. 1A and 1B are respective x-ray and molecular images of a breast.
Figure 1B:
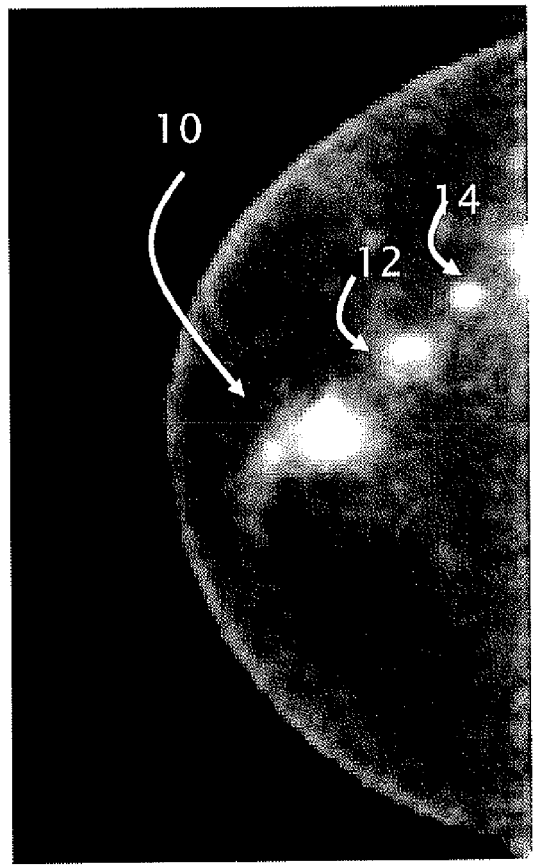
Figure 2:
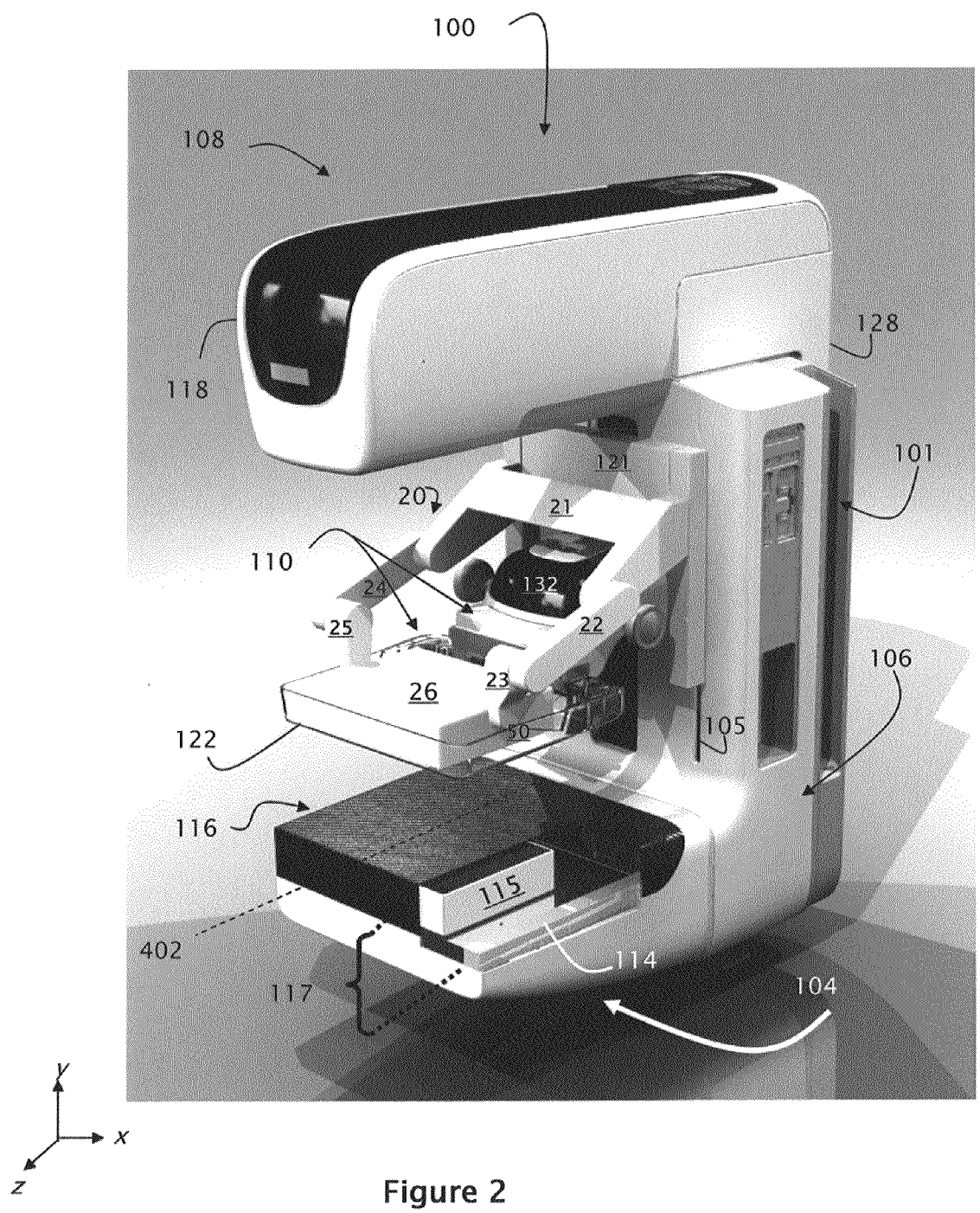
FIG. 2 is an exemplary embodiment of a fused multi-modal three dimensional breast imaging system of the present invention.

FIG. 2 illustrates an exemplary embodiment of an integrated Tomosynthesis/Molecular Breast Imaging (T/MBI) device 100 of the present invention. The T/MBI device 100 integrates x-ray components with molecular imaging components to provide a breast imaging system having increased sensitivity and specificity.

The T/MBI device 100 of FIG. 2 is shown to include a generally C shaped gantry comprised of an x-ray tube assembly 108, a gantry base 106 and a receptor housing 104, each of which is described in detail below. The C-shaped gantry is slideably mounted on a stand 140 (FIG. 12) via tracks 101 for movement along a Y axis to selectively position the gantry for breast imaging.

X-Ray Tube Assembly 108

The x-ray tube assembly 108 includes an x-ray tube head 118 and a x-ray support arm 128. The x-ray support arm is pivotably mounted on the gantry base 106 to enable movement of the x-ray tube head 118 about a horizontal axis 402 for tomosynthesis imaging. For example, during an exemplary tomosynthesis image scan, the x-ray tube head 118 may move from a position of −7.5° to a position of +7.5°. During the tube movement, a total of 15 exposures are performed, each having duration between 30-60 ms. The x-ray tube assembly may also obtain mammograms when the x-ray tube head is positioned at zero degrees.

X-ray tube head 118 includes an x-ray tube (not shown) for generating x-ray energy in a selected range, such as 20-50 kV, at mAs such as in the range 3-400 mAs, with focal spots such as a nominal size 0.3 mm large spot and nominal size 0.1 mm small spot. The x-ray tube target may be comprised of tungsten and/or one or more of technetium, rhodium, ruthenium and palladium. The x-ray tube may include one or more filters such as molybdenum, rhodium, aluminum, copper and tin. In addition, the x-ray tube may include an adjustable collimation assembly selectively for collimating the x-ray beam from the focal spot in a range such as from 7×8 cm to 24×29 when measured at the image plane of an x-ray image receptor included in the system, at a maximum source-image distance such as 75 cm. In one exemplary embodiment, the x-ray tube may be designed with a moving focal spot which counteracts the movement of the x-ray tube during tomosynthesis imaging to reduce image blur, such as is described in U.S. Patent application Ser. No. 61/117,453, filed Nov. 28, 2008 and entitled "Method and system for controlling X-ray Focal spot characteristics for Tomosynthesis and Mammography Imaging," incorporated herein by reference.

Gantry base 106

Gantry base 106 houses motors or other means for controlling the movement of various components of the T/MBI device 100. For example, the gantry base houses a motor (X-ray source control 304, FIG. 3) which controls the movement of the x-ray support arm 128 during tomosynthesis imaging. In addition, the gantry base houses a motor (Compression assembly control 306, FIG. 3) which controls the traversal of a compression assembly 110 along the Y-axis as well as a motor (articulated gamma camera control 302, FIG. 3) that controls the movement of an articulated gamma camera 20.

The compression assembly 110 includes a traversing plate 121, a compression arm 132 and a compression paddle 122 which is releasably coupled to the compression arm 132 via latch 133. In one embodiment, compression paddles of various sizes can be interchanged and positioned properly in the field of view of the image receptor as described in U.S. Pat. No. 7,443,949, entitled "MAMMOGRAPHY SYSTEM AND METHOD EMPLOYING OFFSET COMPRESSION PADDLES AUTOMATIC COLLIMATION AND RETRACTABLE ANTI-SCATTER GRID," owned by the present assignee and incorporated herein by reference. In one embodiment the compression paddle is molded from a radiolucent material and comprises a generally rectangular base from which walls extend to define a compression paddle well 50. The traversing plate 121 moves up and down along slots 105 in the gantry base to control the immobilization or compression of a breast placed between the compression paddle base and a surface 16 of the receptor housing 104. The force used to immobilize or compress the breast may vary in response to a number of different factors, including but not limited to a mode of imaging (x-ray, MBI), a type of imaging (tomosynthesis, x-ray, stereotactic), an angle of imaging (CC or MLO), a size or thickness of a breast, a density of a breast, etc. As the breast is compressed, the compression paddle 122 may be permitted to tilt so that a uniform compression is provided across the entire breast.

According to one aspect of the invention, an articulated gamma camera assembly 20 is also mounted to the traversing plate 121. The articulated gamma camera assembly 20 includes a support brace 21, a pair of jointed arms 22 and 24, camera mounts 23 and 25 and gamma camera 26. The gamma camera is essentially a photon detector which counts and images photons emitted from decaying radioisotopes which have been injected into the breast (either single or dual photon emitting isotopes as will be described later herein). The jointed arms 22 and 24 are coupled to the support brace 21 and camera mounts 23 and 25 by motorized gears which control the advancement of the gamma camera 26 into an imaging position (shown in FIGS. 2 and 11) and the retraction of the gamma camera 26 into a retracted position (shown in FIG. 10). In one embodiment when the articulated camera is placed in the imaging position it rests within the compression paddle well 50 such that an imaging face of the camera 26 remains flush against the rectangular base of the compression paddle as the paddle compresses or otherwise immobilizes the breast The jointed arms 23 and 24 enable the camera to remain flush against the paddle even when the paddle tilts during compression.

In another embodiment, the gamma camera need not remain flush in the compression plate well, but rather may be pivoted to any angle around an axis defined by the camera mounts. The pivoting may be manually controlled or motorized. The ability of the articulated gamma camera to pivot freely in this manner allows for improved imaging of the chest wall or axilla tissue. In still a further embodiment, the articulated arms of the gamma camera may be positioned not at the sides of the camera, as shown in FIG. 2, but closer towards the center of the gamma camera. In a representative embodiment, the pair of arms may be replaced with a single articulated arm which is coupled to a mount on the top (non-imaging) surface of the gamma camera, allowing the camera to be pivoted in three dimensions.

As mentioned above, the articulated arms control the advancement of the camera towards an imaging field, and the retraction of the camera away from the imaging field. In one embodiment, the motion of the camera from the retracted to the position to the advanced position is controlled such that the leading edge of the camera (i.e., the edge facing the patient) travels along an underhanded arc path (as indicated by the arrow 1200 in FIG. 10). Introducing the gamma cameras into the imaging field in this manner keeps the camera below the line of vision of the patient and may therefore reduce patient anxiety. The camera may be retracted from the imaging field with a leading edge (the edge facing away from the patient) travels in a generally underhanded arcuate path towards the device, also indicated by the arrow 1200 of FIG. 10. Of course other methods of introducing the camera into the imaging field, including lowering the camera into the field on a track or from a pivot point, may be substituted herein without affecting the scope of the present invention in one embodiment, the movement of the camera 26 is synchronized with the movement of gamma camera 115, although this is not a requirement of the invention and other embodiments wherein the cameras are independently advanced and retracted are within the scope of the present invention.

Receptor Housing 104

The receptor housing 104 is an enclosed housing for the detector subsystem of the T/MBI device. As mentioned above, an upper surface 116 of the housing 104 serves as a breast compression plate, or bucky. FIG. 2 includes a cut away view of the receptor housing provided solely for the purpose of describing the internal detector subsystem 117. The detector subsystem includes at least a retracting gamma camera 115 and a full field digital detector 114. The retracting gamma camera 115 is a photon detector which counts photons emitted from decaying radioisotopes which have been injected into the breast (either single or dual photon emitting isotopes). The full field digital detector 114 is an x-ray detector such as the amorphous selenium digital detectors described in U.S. Pat. Nos. 7,122,803, 7,233,005 and 7,304,308 owned by the assignee of the present invention and incorporated herein by reference. It should be noted that the present invention is not limited to systems which use amorphous digital detectors, and other detectors such as scintillating detectors may be substituted herein without affecting the scope of the invention. In one embodiment, the digital detector is adapted for movement within the receptor housing; for example, the digital detector 114 may move laterally or pivot about one or more points during tomosynthesis imaging. Such movement of the detector may be controlled by a rotate/retract control motor 310 (FIG. 3) located within the gantry base 106.

Figure 3:
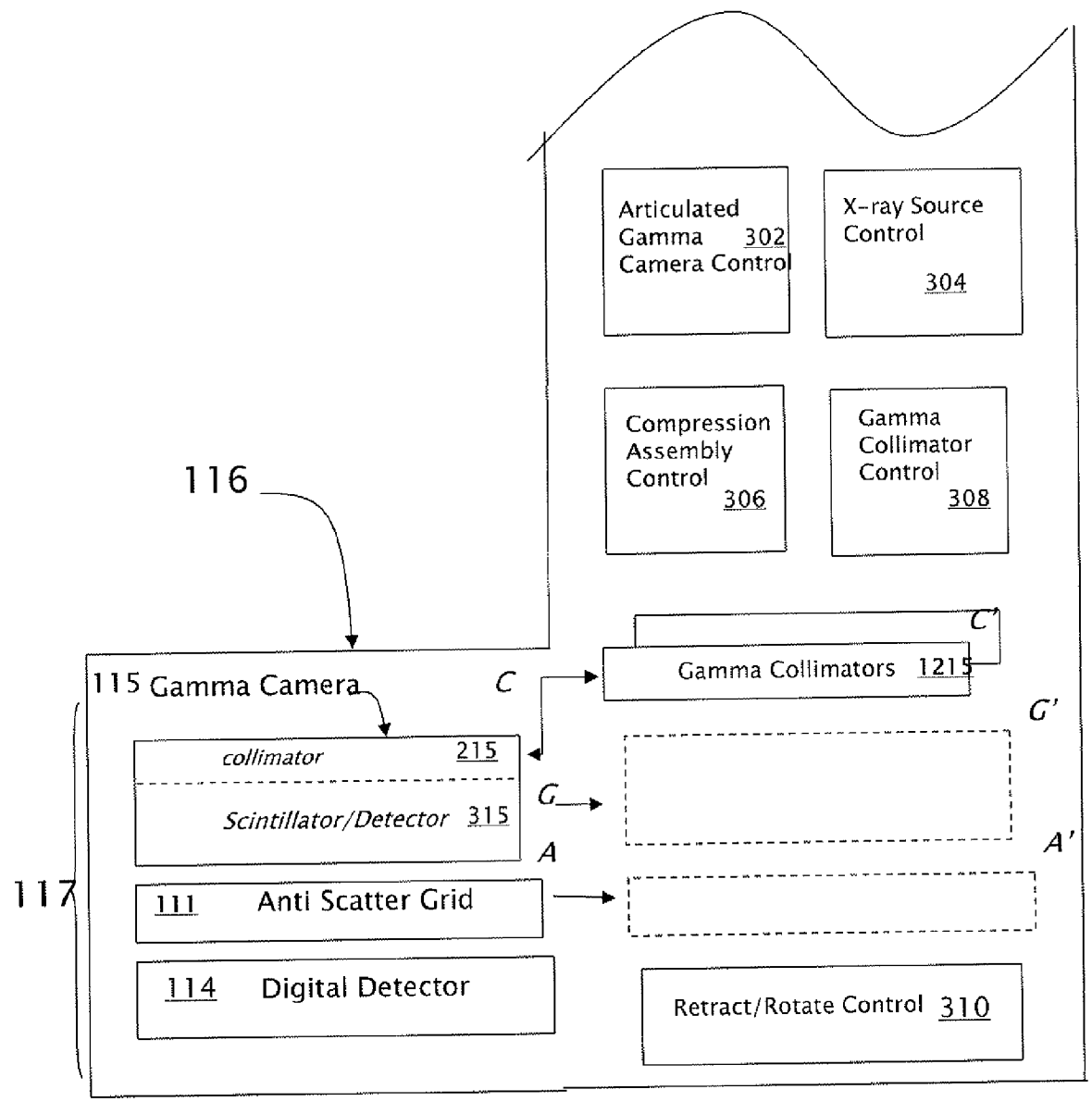
FIG. 3 is a block diagram of a cross section of the gantry base and receptor housing of the device of FIG. 2.

FIG. 3 is a block diagram of a cross-section of the receptor housing 104 and a portion of the gantry base 106 illustrating the detector subsystem in greater detail. As mentioned above, the gantry base houses several control systems (302-310).

Although the control systems are represented in the figures as discrete functional blocks it should be recognized that such delineations are provided merely to facilitate the description of the device and not by way of limitation; it is appreciated that there are numerous different but equivalent ways that the functionality may be combined and embodied that are within the scope of the present invention.

An anti-scatter grid 111 is shown positioned between the detector 114 and the gamma camera 115. As described in U.S. Pat. No. 7,443,949, referenced above, the anti-scatter grid is positioned over the digital detector 114 (in position A) during mammography, to reduce x-ray scatter. The anti-scatter grid may be withdrawn for tomosynthesis and/or other x-ray imaging, preferably via motorized retraction of the anti-scatter grid (to position A') in the gantry base as indicated by dashed line in FIG. 3.

According to one aspect of the invention gamma camera 115 is withdrawn from the x-ray imaging field of view prior to x-ray imaging. In one embodiment, the gamma camera may be withdrawn by retracting the camera 115 into the gantry base 106. For example, gamma camera 115 may be positioned at location G during molecular imaging, but moved to position G' for x-ray imaging. The retraction of the gamma camera 115 may be motorized, or alternatively may be achieved through manual means (i.e., via a manual lever to slide the camera into the housing). In another embodiment, the gamma camera may be withdrawn from the x-ray imaging field of view by removing the camera from the device 100, for example by ejecting the camera or otherwise extracting the camera from at least part of the housing 104.

As will be described in more detail later herein, the gamma camera may also be rocked or rotated around one or more pivot points, or moved laterally or vertically for molecular imaging. For example it may be desirable to rotate the camera towards the patient to better image the chest wall or axilla tissue. The receptor housing is therefore of sufficient size to house the gamma camera 115, anti-scatter grid 111 and digital detector 114 and to allow movement of both the digital detector as well as the gamma camera. The movement of the gamma camera may also be controlled by the rotate/retract controller 310.

According to one aspect of the invention rotate/redaction control further includes functionality for motorized retraction of a collimator 215 of a gamma camera (for example by moving the collimator from position C to C') or otherwise withdrawing the collimator from the molecular imaging field. For example, like the anti-scatter grid, the collimators may be moved into the gantry base (either by motor or manually) or may be ejectable. In still another embodiment, the bucky surface 116 may be hinged to permit manual access to the collimators of the gamma cameras, to allow the collimators to be swapped, exchanged, flipped or otherwise modified. The ability to retract or otherwise remove the collimator in this manner allows a single gamma camera to be used for molecular imaging using both Single Positron Emission radioisotopes as well as Positron Emission radioisotopes.

The functionality may also be adapted provide motorized exchange a collimator that is disposed over a scintillator/detector structure 315 of the gamma camera with different collimator selected from a group of alternative collimators 1215 stored within the housing. The collimator may be of a different type, or of the same type but having different angular collimations. The ability to exchange collimators in this manner allows the radiologist to customize the camera in accordance with a desired view. In still another embodiment a programmable collimator capable of selective modification the collimation angle may be used for custom imaging.

In still yet another embodiment, the gamma camera can be tilted at varying angles during the acquisition. For example, the gamma camera 26 can be moved away from paddle 122 sufficiently to allow angulation of the gamma camera and so acquire views of the breast with different angles and therefore acquire information that can be used to perform a reconstruction such as SPECT or tomosynthesis view of the distribution of radiopharmaceuticals. In this mode, the gamma camera would be placed in a given orientation relative to the breast, and an image acquired for a time inverval. The gamma camera would then be positioned in an different orientation and a second image acquired. Multiple images of the breast are then acquired and these are used in the reconstruction.

X-Ray Imaging

As mentioned above, the T/MRI device is capable of performing both X-ray and molecular breast imaging. During x-ray imaging x-rays emitted from an x-ray source are directed at a body part to be imaged. The x-rays penetrate the body part and are attenuated differently depending upon the structures that they encounter. An x-ray detector on the underside of the body part records the resultant x-ray energy, providing a pictorial representation of the x-ray attenuation and associated anatomical structure of the body part.

In one embodiment, the x-ray system may be configured for mammographic imaging at multiple views (cranio-caudal (CC) and mediolateral oblique (MLO)), tomosynthesis imaging and stereotactic imaging. During mammogram acquisition, the compression paddle can shift automatically depending on the view to be acquired. For example, the paddle can be centered on the x-ray receptor for a CC view, shifted to one lateral side of the receptor for an MLO view of one breast and to the other lateral side of the receptor for an MLO view of the other breast. In one embodiment, the size and shape of the paddle can be automatically recognized by the system when mounted so that the shifts can be adjusted to the type of paddle. The mammographic images (Mp) are captured as two-dimensional images which may be stored and/or immediately displayed to the radiologist.

During tomosynthesis the breast is compressed and a plurality of tomosynthesis projection images (Tp) are acquired at respective angles relative to the breast. A variety of systems are provided in the art for acquiring breast tomosynthesis image data. The systems may vary in the number of projection images that are obtained and the angles at which the images are taken, in the path that the x-ray source takes when obtaining the projection images (arcuate, linear, sine-wave motion, etc.), in a motion of the digital detector (i.e., rocking, rotating, linear movement) and in reconstruction techniques (back-projection, weighted back-projection, etc). The present invention may incorporate any such tomosynthesis system.

The projection images are reconstructed into a plurality of tomosynthesis reconstructed images Tr representative of breast slices that have selective thicknesses. Any of the Tp, Tr and Mp images may be displayed individually or simultaneously on a display screen as described in U.S. patent application Ser. No. 11/827,909 entitled IMAGE HANDLING AND DISPLAY IN X-RAY MAMMMOGRAPHY AND TOMOSYNTHESIS, incorporated herein by reference. Simultaneous viewing of the images may be performed in a variety of ways, including but not limited to overlaying one image on another, and toggling between individual or overlaid images or using cine mode, or having one image displayed as an inset in another images. Additionally, the two images may be blended together, or a visual slide bar may be provided such that, as the bar slides over the image, the image morphs from an image taken in a first modality to an image taken in a second modality, where the modality may be an x-ray modality (i.e., mammogram or tomosynthesis image) a PET or SPECT image.

Molecular Breast Imaging

Two types of molecular breast imaging include Single Photon Emission Tomography (SPECT) and Positron Emission Tomography (PET). In both forms, the body part to be imaged is injected with a radioisotope/radiopharmaceutical. Cancerous cells tend to absorb higher amounts of the radioisotope than non-cancerous cells and therefore the radioisotope collects in areas of cancerous lesions in the breast. As the radioisotope decays, gamma rays are emitted from the radioisotope. The gamma rays are recorded by gamma cameras, which essentially count the photons in the gamma rays. Those areas of the breast which have absorbed the largest amounts of radioisotope will emit the largest number of gamma rays and have the highest photon counts in the resultant image. The quality of the image is dependent upon both the radioisotope and the gamma camera.

Figures 4A, 4B:
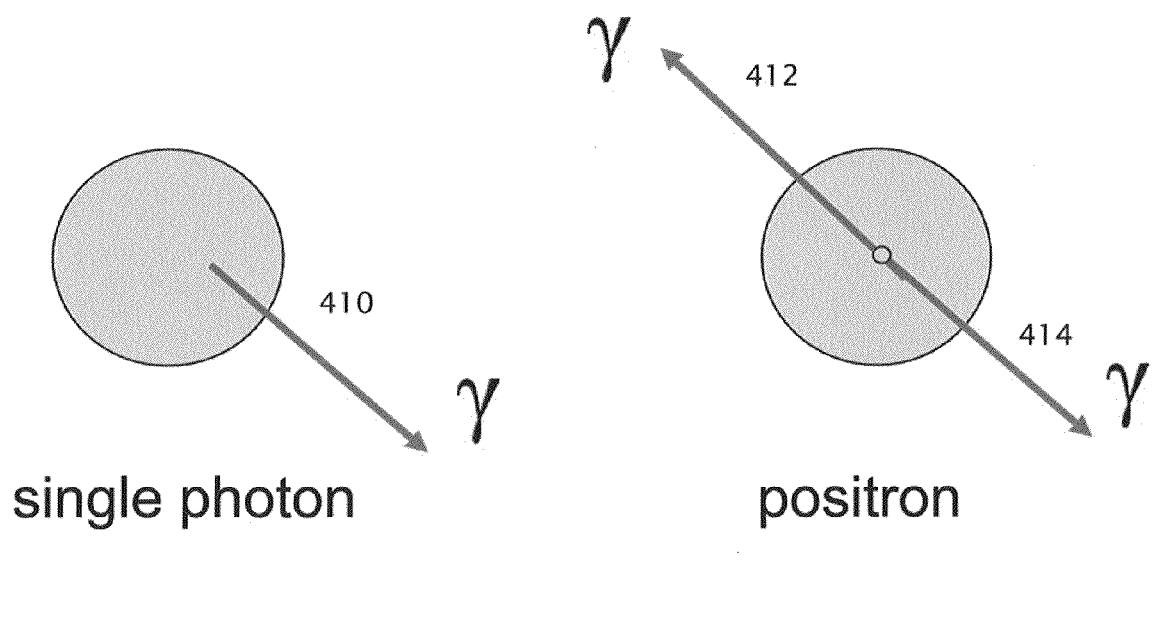
FIGS. 4A and 4B are diagrams illustrating gamma ray dispersion from single-photon and positron radioisotopes.

One difference between SPECT and PET lies in the radioisotope that is used for imaging. For example, as shown in FIG. 4A, single photon gamma emitters used in SPECT emit a single gamma ray 410 of energy 80-167+ keV emitted from each decay. Single Photon radioisotopes include, for example, TC-99 mm (found in Sestamibi), TI-201 (Found in Thallus Chloride), Xe-133 (Gas), I-123 (IMP), Co-57 (physics), etc. Dual photon Positron Emission Technology (PET) radioisotopes simultaneously emit dual, co-linear gamma rays 412, 414 of energy 511 keV each. Examples of PET radioisotopes include the F-18 isotope which can be found in FDG.

Figure 5A:
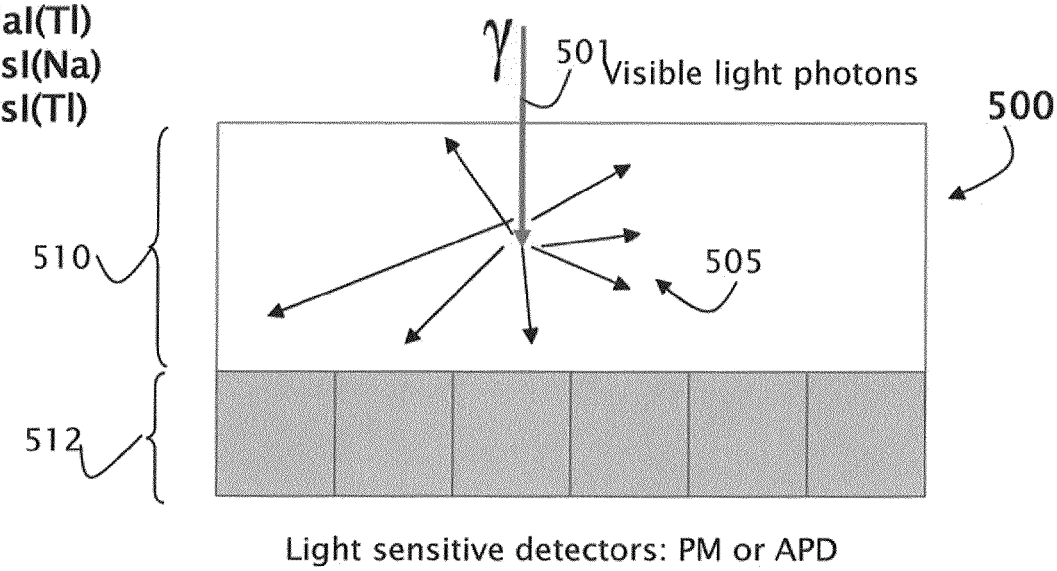
FIGS. 5A and 5B illustrate various embodiments of gamma detectors which may be included in the Tomosynthesis/Molecular Breast Imaging (T/MBI) device of the present invention.
Figure 5B:
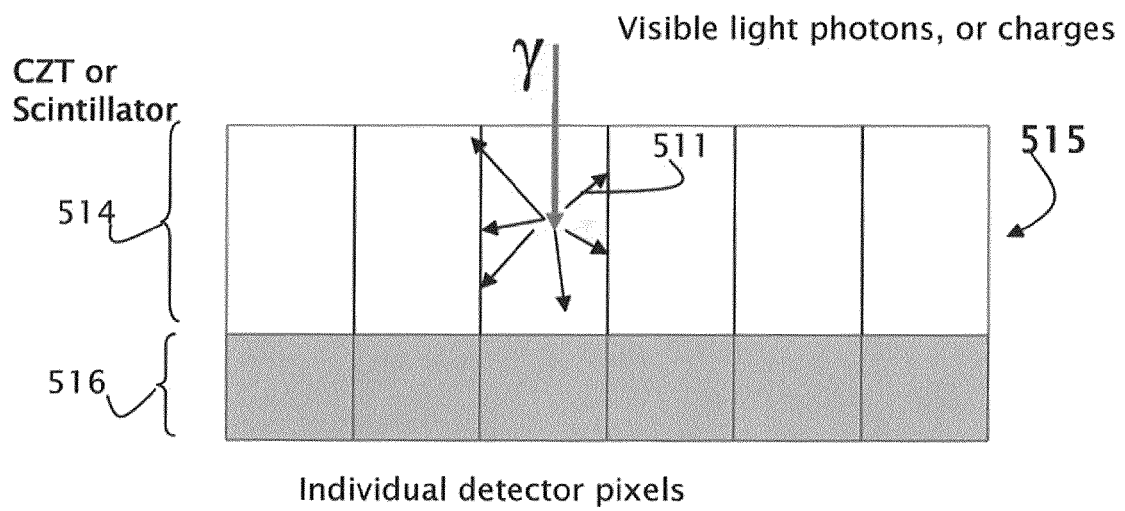

FIGS. 5A and 5B illustrate two different embodiments of gamma detector which may be incorporated into the T/MBI device of the present invention for PET imaging. FIG. 5A illustrates an Anger type gamma detector 500 comprised of a scintillator layer 510 and a visible light detector layer 512. Visible light rays 505 are generated when a gamma ray 501 strikes the scintillator. The detectors in layer 512 detect the visible light rays, with the relative signals of the detectors indicating the location of origin of the gamma ray. Figure 5B illustrates a discrete gamma detector 515 which may be used for PET imaging and includes separate scintillators 514 for each detector 516. When a gamma ray strikes the scintillator layer, resulting visible light photons or charges 511 will only impact a single detector.

Figure 6:
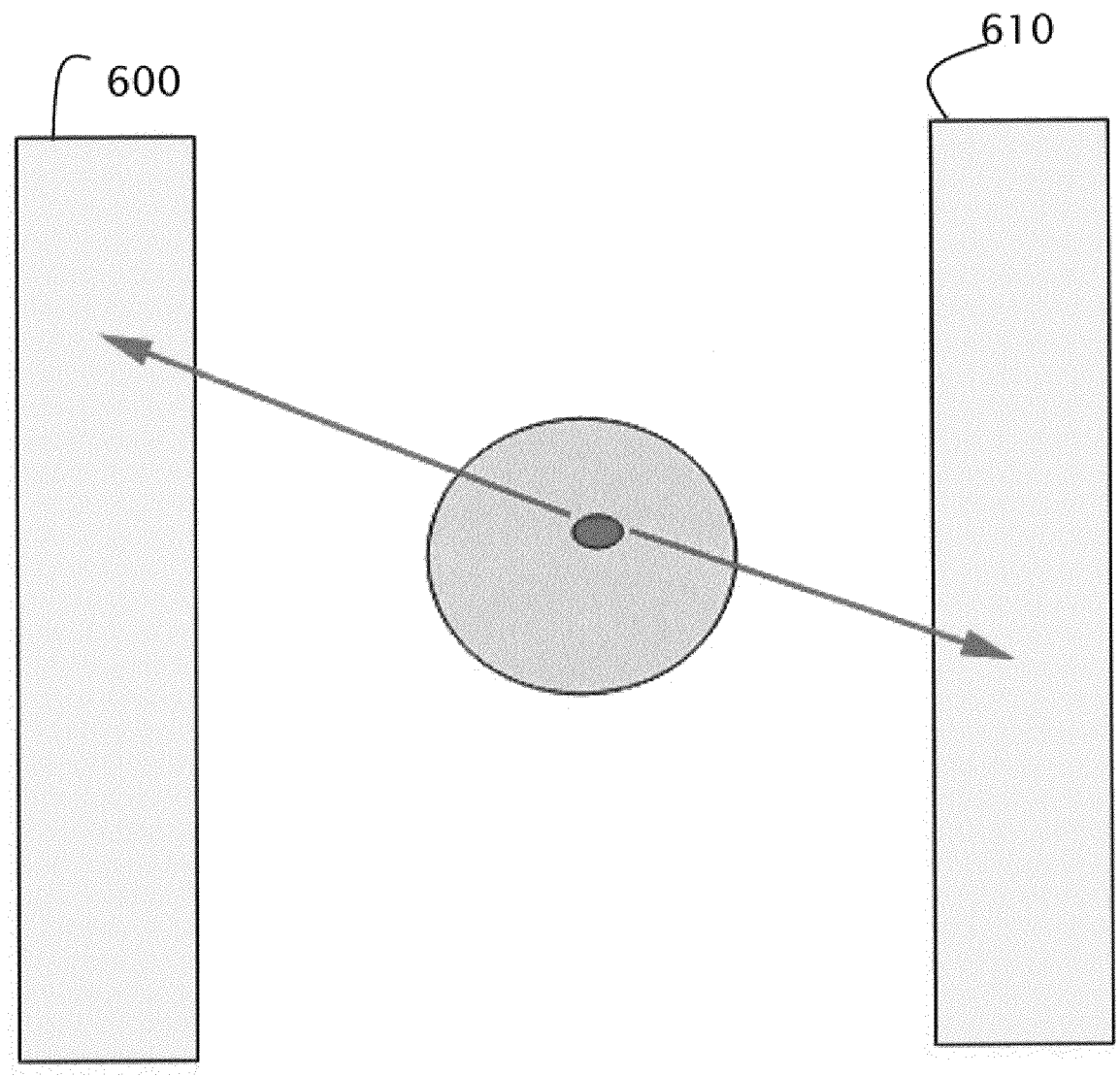
FIG. 6 illustrates the positioning of gamma cameras and flow of gamma rays during Positron Emission Tomography (PET) imaging.

Referring now to FIG. 6, during PET imaging two opposed PET gamma cameras such as camera 600 and 610 record the gamma emissions. Using information such as the known spacing of the cameras, the location of the lesions in three dimensional space may be readily determined and used to reconstruct a three-dimensional image PET-MBIr. According to one aspect of the invention, this three-dimensional image may be viewed as two dimensional slabs of selectable thickness together with x-ray images (Mp, Tp, Tr) on a display. The PET-MBIr images may be viewed side by side with the x-ray images, overlaid with one or more of the x-ray images for toggling between the images of viewing in cine mode, or one of the PET-MBIr or X-ray images may be inserted in a thumbnail view in the other image.

Figure 7:
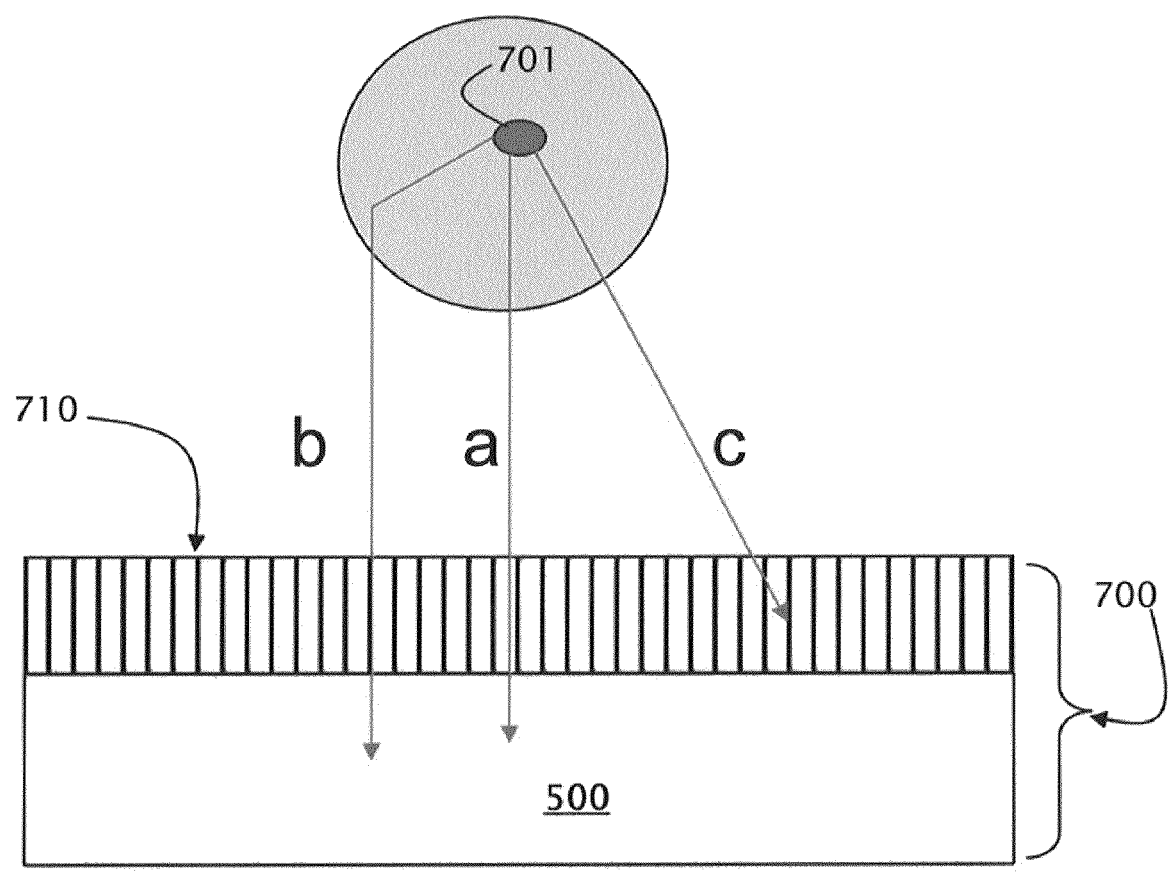
FIG. 7 illustrates a general structure of a single photon planar gamma camera that may be integrated into the T/MBI device of the present invention.

Single photon imaging involves detecting the individual photons that are emitted during decay by using a gamma camera. Photons can emerge unscathed, or can scatter. If the photon scatters, the energy changes. In order to determine where the photon emerged from and to ensure that scattered energy is not erroneously recorded, gamma cameras generally include collimators. FIG. 7 illustrates exemplary gamma camera 700, which may include one of the gamma detectors of FIG. 5A or 5B (such as detector 500) and a collimator 710. The collimator essentially filters out scatter, for example causing contributions of rays b and c (emitted from lesion 701) to be rejected or ignored. Three dimensional gamma images, often called Single Photon Emission Computed Tomography (SPECT) are formed by acquiring multiple images from a gamma camera, with each image acquired by having the gamma camera arranged at different angles relative to the object being imaged.

Figure 8:
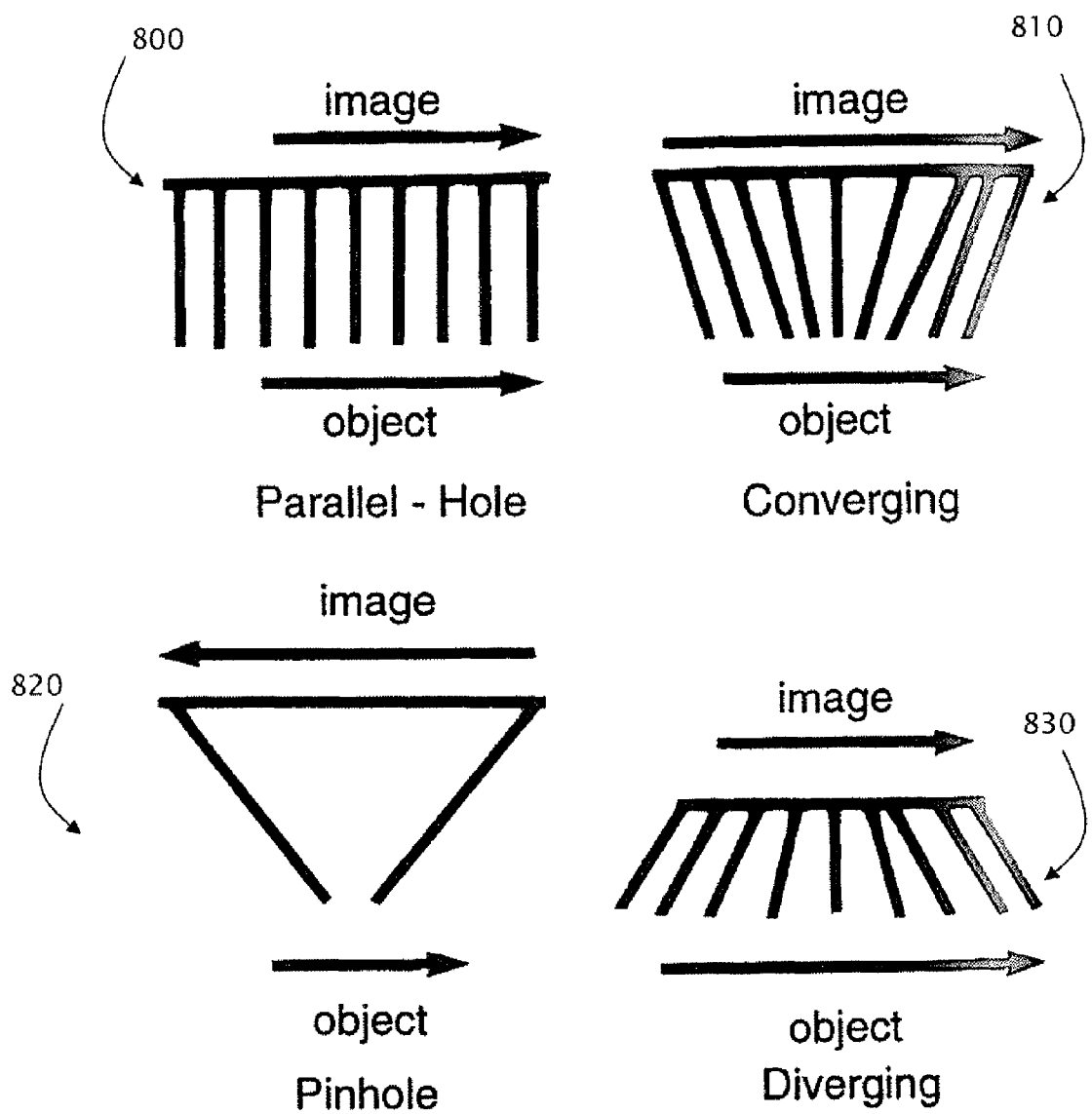
FIG. 8 illustrates various collimators that may be used with the gamma camera of the present invention.

Collimators are generally formed as holes lead, foil stamped lead or tungsten or lead casts. FIG. 7 illustrates a general parallel hole type collimator although other types of collimators may be used for different breast imaging needs. For example, slanted collimators may be used to provide Z position measurement for either lesion or biopsy needle with radiotracers. FIG. 8 illustrates various types of collimators that may be included as part of the T/MBI device 100, including a parallel hole collimator 800, a converging collimator 810, a pin hole collimator 820 and a diverging collimator 830. As mentioned above with regard to FIG. 2, the collimators may be stored within or near the device 100, and swapped as needed. More details regarding how different collimators may be used to provide improved chest wall and axilla tissue coverage, as well as for three-dimensional lesion localization and biopsy is described later herein.

The SPECT camera operates similarly to a two dimensional digital detector, capturing a two dimensional projection image SPECT-MBIp of gamma radiation during each exposure period. A plurality of projection images SPECT-MBIp can be obtained by moving the SPECT camera to different angular positions relative to the imaged object and collecting photon information for the exposure period. In a system such as the T/MBI system which includes multiple gamma cameras one or both cameras may be moved through angular ranges to capture different projection images for each exposure period. A three-dimensional volume may be reconstructed from the projection images using techniques such as those described in U.S. Pat. No. 5,359,637 entitled Self-Calibrated Tomosynthetic, Radiographic Imaging System, Method and Device, by Weber, incorporated herein by reference, to provide a three-dimensional reconstructed data set SPECT-MBIr. According to one aspect of the invention, this three-dimensional data set may be viewed as two dimensional slabs of selectable thickness together with x-ray images (Mp, Tp, Tr) on a display. The SPECT-MBIr images and SPECT-MBIp images may be viewed side by side with the x-ray images, overlaid with one or more of the x-ray images for toggling between the images of viewing in cine mode, or one of the SPECT-MBIr or X-ray images may be inserted in a thumbnail view in the other image.

Workflow

Figure 10:
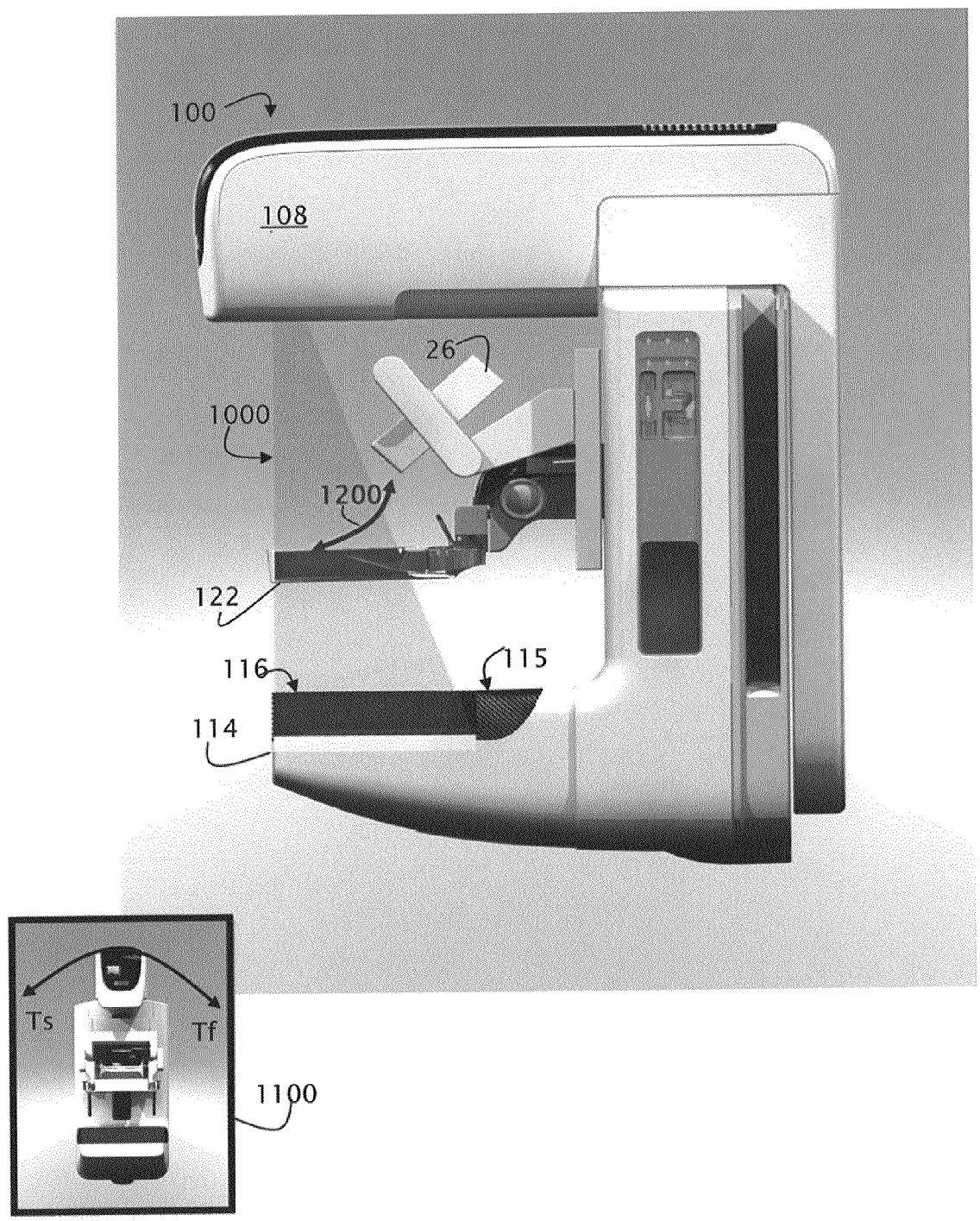
FIG. 10 illustrates an embodiment of the T/MBI device of the present invention with gamma cameras retracted to eliminate interference during tomosynthesis imaging.
Figure 11:
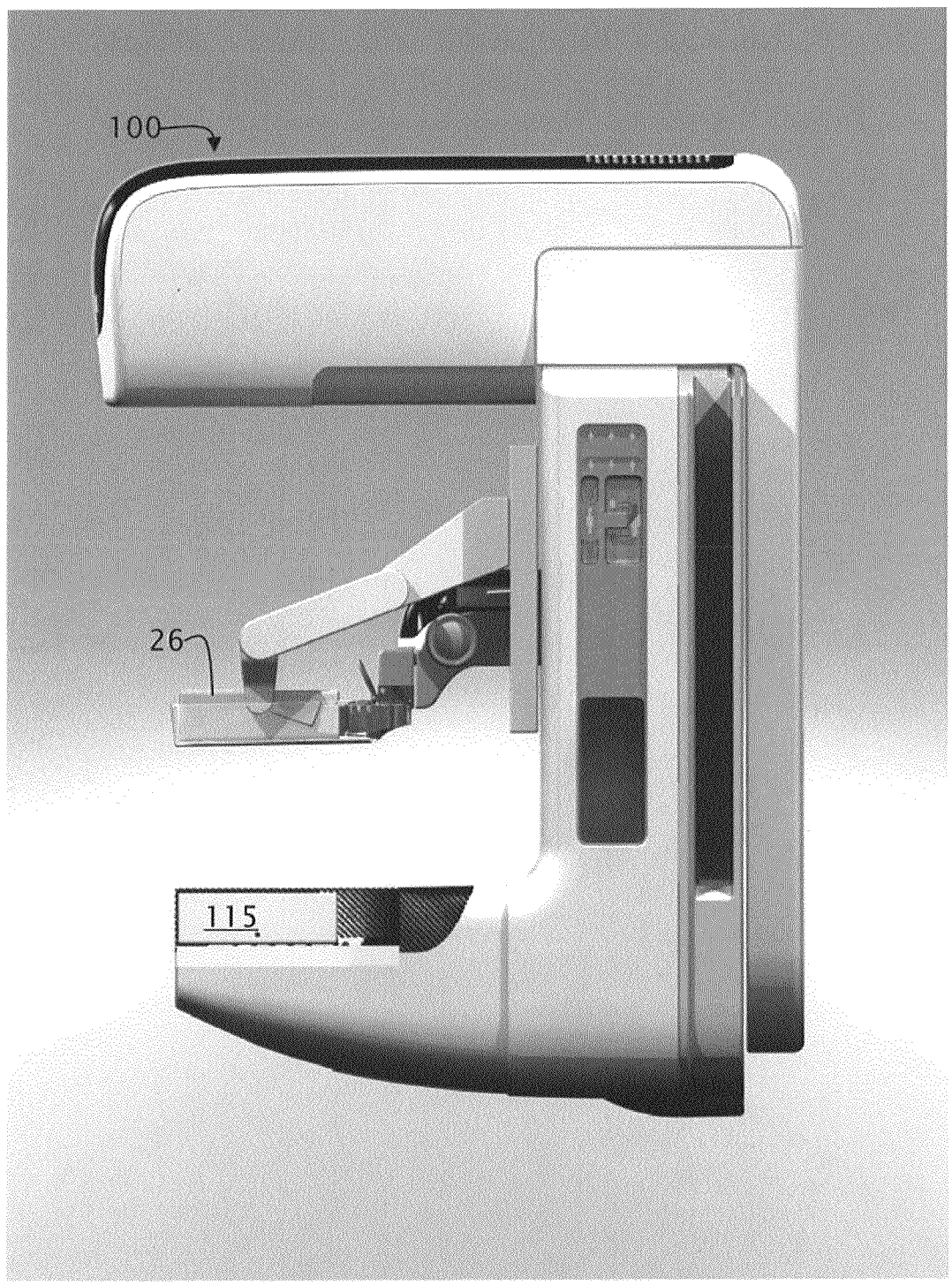
FIG. 11 illustrates an embodiment of the T/MBI device of the present invention with gamma cameras positioned for molecular imaging.

Having described exemplary components of the T/MBI system, an exemplary workflow 900 that may be performed to capture both tomosynthesis and molecular images with a single breast compression will now be described with regard to the flow chart of FIG. 9 and the images of the device 100 shown in FIGS. 10 and 11. At step 910 a radioisotope is injected into the breast. At some point thereafter and in accordance with the half life of the isotope, the breast is ready for imaging. At step 912 the breast is compressed between the compression paddle and the bucky 116. At step 914 a tomosynthesis scan is initiated and the x-ray source traverses along a path from position Ts to Tf as shown in inset 1100. As the x-ray source traverses along the path a number of x-ray projection images are obtained. As shown in FIG. 11 during x-ray imaging the gamma cameras 115 and 26 are withdrawn such that they do not encroach upon the x-ray field 1000 or block the detector 114. In some workflows, a CC mammogram view may be obtained following the tomosynthesis scan. In such instances the anti-scatter grid will extend over the detector 114 prior to imaging.

Figure 9:
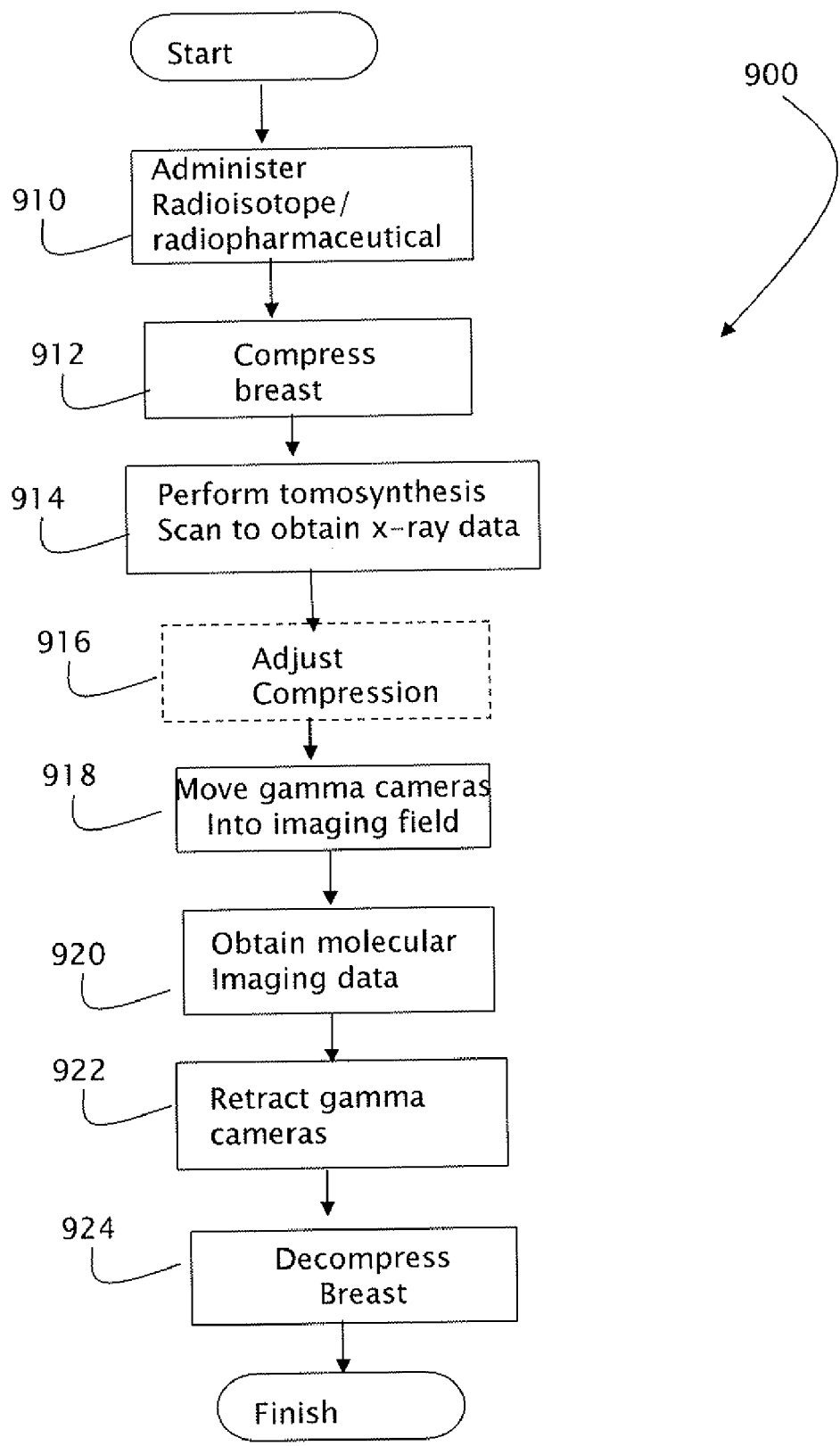
FIG. 9 is a flow diagram of exemplary steps that may be performed during a combined tomosynthesis/molecular imaging process of the present invention.

In the process of FIG. 9 a molecular image is obtained following the tomosynthesis scan without full breast decompression. At step 916 the compression of the breast may be adjusted for the molecular scan. It is not a requirement to adjust the breast compression, and thus the step is shown in dashed lines to indicate its optional nature. At step 918 the gamma cameras are moved into position. In one embodiment the gamma camera 26 moves along path 1100 until it rests flush in the compression paddle well as shown in FIG. 11. Gamma camera 115 is moved out of the gantry base into position. In certain gamma camera or SPECT embodiments, only one gamma camera or SPECT camera may be provided for positioning. Advantageously the movement and positioning of the cameras is computer controlled. For example in some embodiments the cameras may differ in size from each other and/or the digital detector. The cameras may be positioned in response to the detection of suspicious artifacts identified during the tomosynthesis screen so that the cameras are centered on any suspicious artifact, or may be positioned at angles to capture the axilla tissue or better image the chest wall. The positioning of the gamma cameras may be automatic, for example in response to CAD screening of the tomosynthesis data, or may be controlled via user input.

At step 920 molecular image data is obtained. For embodiments that use PET cameras the PET image is obtained by positioning the PET camera pair around the breast for an exposure period. As described above, to obtain 3-D image data using SPECT cameras, the camera(s) may be moved to multiple positions for a defined set of exposure periods. At step 922, when molecular imaging is complete gamma camera 26 may be retraced along the path indicated by line 1100 in FIG. 10, and the breast decompressed at step 924. Assuming that radioisotope was administered to both breasts, steps 912-924 may be repeated with the alternate breast.

One embodiment shows sequential use of the imaging modalities. This will include the x-ray image acquired before the nuclear image. It is also possible to reverse the order of the acquisitions, and perform the nuclear acquisition before the x-ray image.

The T/MBI device however is not limited to sequential use of the imaging modalities. Rather the provision of different imaging modalities in a single device enables a radiologist to tailor the workflow based on the particular need of the patient. For example when dealing with patients with dense breasts which will x-ray with low sensitivity, the device allows the radiologist to forego an x-ray in favor of obtaining a molecular image.

It should further be noted that there is no requirement that MBI imaging have a fixed exposure period. For example, a workflow is envisioned by which the entire breast is imaged at low resolution for a short period to identify areas of high uptake. A subsequent exposure may be obtained by imaging just the identified region at higher resolution, using a converging collimator or pinhole collimator, for example, or by moving the camera in space to center the camera upon the region of interest.

Figure 12:
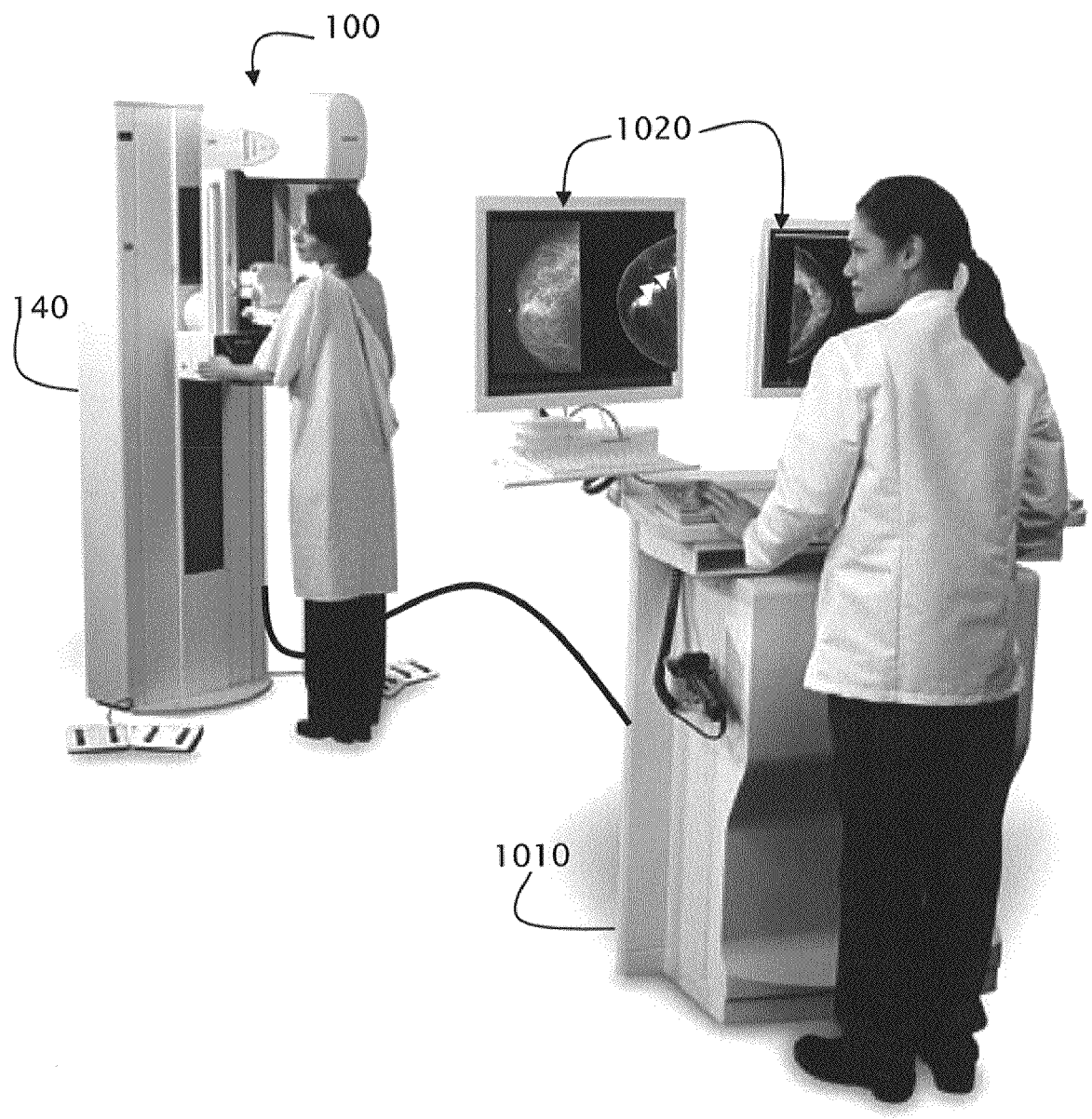
FIG. 12 illustrates the T/MBI device in a radiology suite.

FIG. 12 illustrates the use of the T/MBI device in a radiology suite. The device 100 may be mounted on a stand 140 for patient height positioning. The device 100 may be coupled to a workstation 1010, enabling a radiologist to store and review images on display 1020. As mentioned above the images from the any of the imaging modalities including x-ray mammogram images, tomosynthesis images and molecular images may be displayed either individually or simultaneously as projection images or reconstructed images. The images may be displayed side by side, or overlaid. Controls at the workstation will enable the radiologist to toggle between two-dimensional projection images, the three dimensional reconstruction or slices from the same or different modality. In addition the reviewer may access, either at the workstation or via a separate workstation, Computer Aided Diagnosis tools which provide visual indicators of regions of interest on the images. In one embodiment, CAD results that are obtained from one modality may be overlaid on images from the second modality; for example mammography CAD results may be overlaid on MBI images or tomosynthesis slices, tomosynthesis CAD results may be overlaid on mammography or MBI results or MBI CAD results may be overlaid on any x-ray images. In still a further embodiment, CAD results are generated based on input from both imaging modalities.

Dual Head MBI features

As mentioned above, the device is not limited to breast screening or diagnostic use or to use in combination with the x-ray imaging components. According to one aspect of the invention, it is realized that improved three-dimensional lesion localization and biopsy capability can be provided using a dual-head molecular breast imaging technology that is capable of modifying the collimation of the gamma rays. The dual-head MBI device may be part of the integrated T/MBI device 100 (which, as described with regards to FIG. 3 may change the collimators that are used with the gamma detector), or may be provided as a discrete dual-head MBI device.

Figure 13:
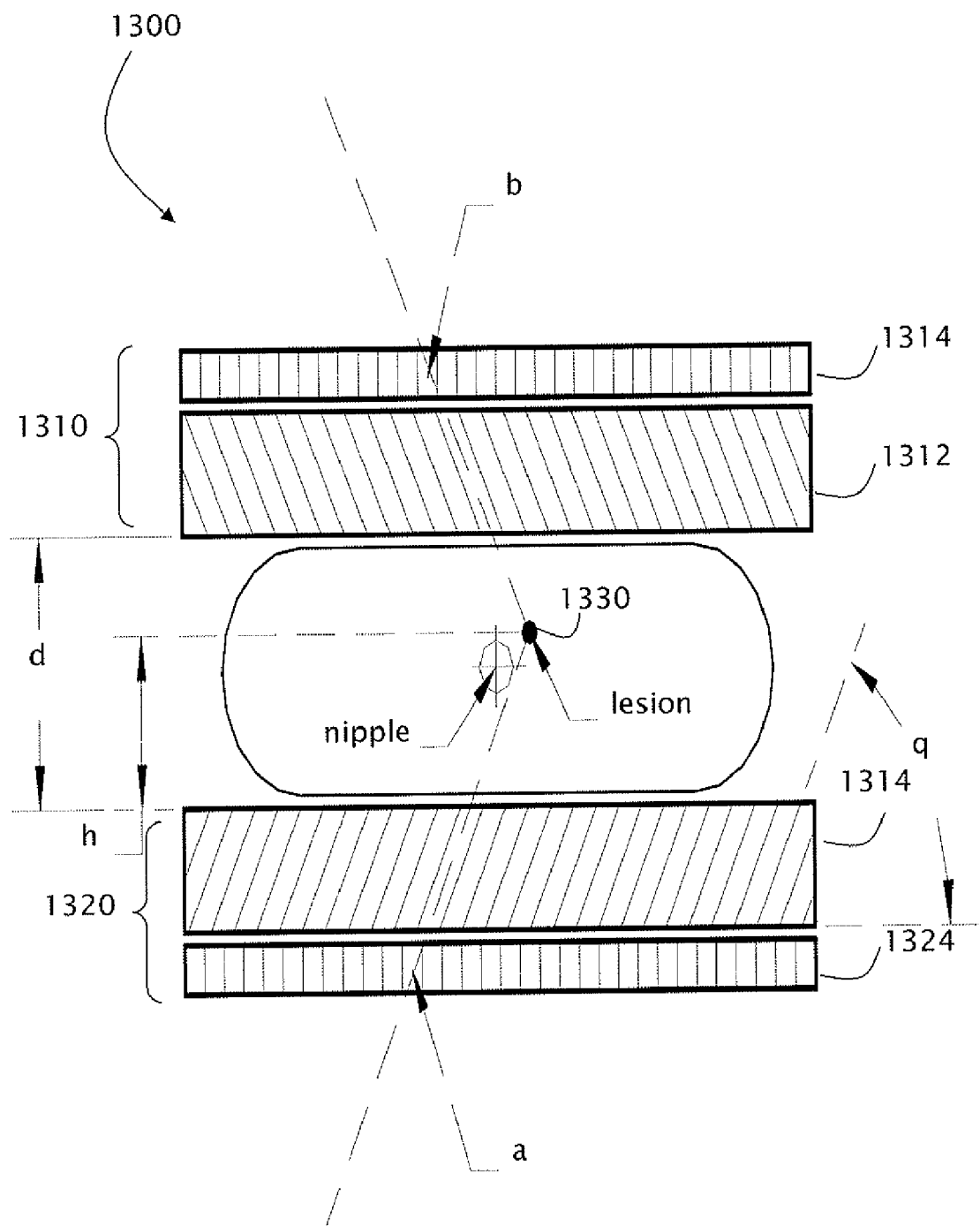
FIG. 13 illustrates a dual head molecular breast imaging system including slanted collimators.

For example FIG. 13 illustrates a dual head MBI imager 1300 having an upper gamma camera 1310 and a lower gamma camera 1320, and obtaining a cranio-caudal (CC) image of the patient's breast. The upper camera includes a detector 1314 and a collimator 1312, while the lower camera includes detector 1324 and collimator 1322. According to one aspect of the invention, the collimators 1312, 1322 are both slanted collimators which are positioned adjacent and parallel to each other, with the slant of collimator 1312 being a mirror image of the slant of collimator 1322. The slants assist in determining the Z location of the lesion 1330 as follows. As the radioisotope decays, gamma rays will be emitted from lesion 1330. The rays are detected at the detector in location b of the upper camera 1310 and at the detector in location a of the lower camera 1320. With a collimator slant angle of known value "θ", a known value "d" of the distance between the cameras (and associated breast thickness), the lesion location "h" is derived using equation I below:

$$h = \frac{d}{2} + \frac{1}{2} * \frac{a-b}{\tan\theta} \quad \text{Equation 1}$$

This equation can be understood conceptually very easily. The location on the gamma camera a and the angle of the collimator holes allow one to determine the trajectory line that the photon travelled along to result in an image at location a. Similarly for the other gamma camera location b, one can determine the trajectory line. The intersection of these two lines determines the point in three-dimensional space where the lesion is located.

Figures 14A, 14B:
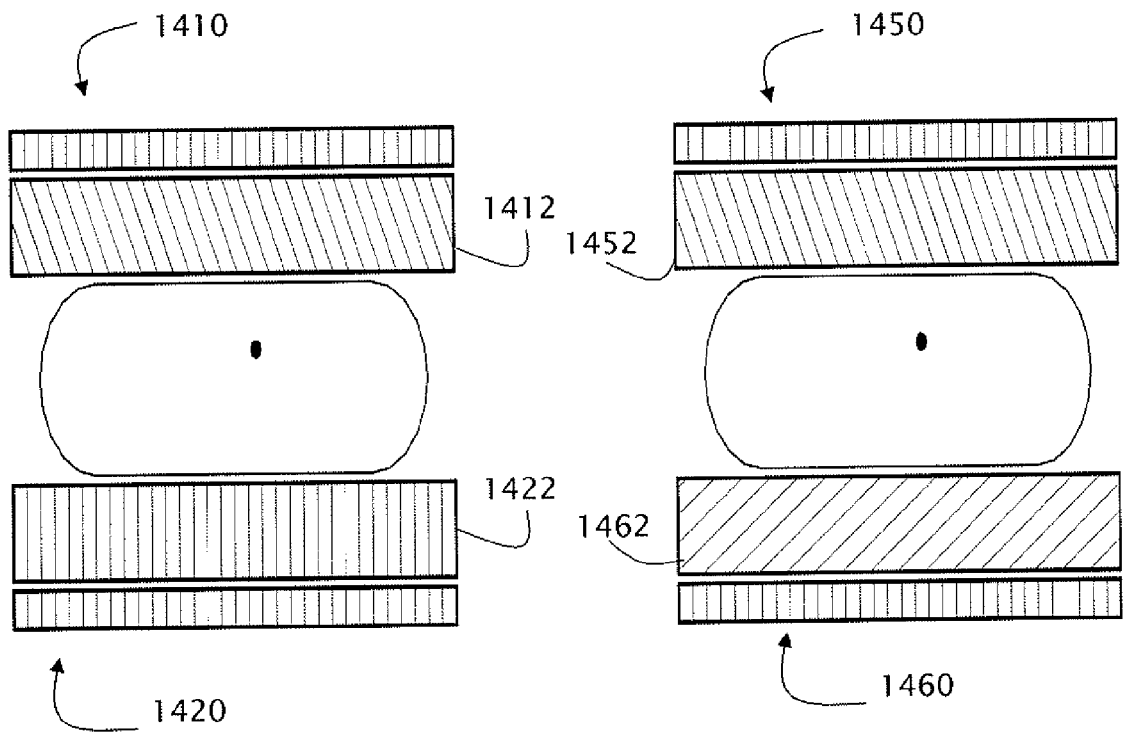
FIGS. 14A and 14B illustrate alternative collimator arrangements that may be used for lesion detection.

FIGS. 14A and 14B illustrate alternate embodiments of gamma cameras, wherein the collimators 1412 and 1410 differ in that collimator 1412 is a slant collimator of angle "θ" while the collimator 1422 is a parallel through hole collimator The collimators of cameras 1450 and 1460 differ in that collimator 1452 is slanted at a different angle than the collimator 1462. In both instances, the corresponding lesion height can be derived using equations similar to that of Equation I but taking into account the relative difference in collimation angles.

Providing slanted collimators in a dual-head gamma MBI system can increase the imaging coverage of the system. When performing conventional x-ray breast mammographic imaging, breast tissue outside the compression assembly is not visible in the resulting image. However, using a dual-head gamma camera with slanted collimators permits active imaging of axilla and chest tissue.

Figure 15:
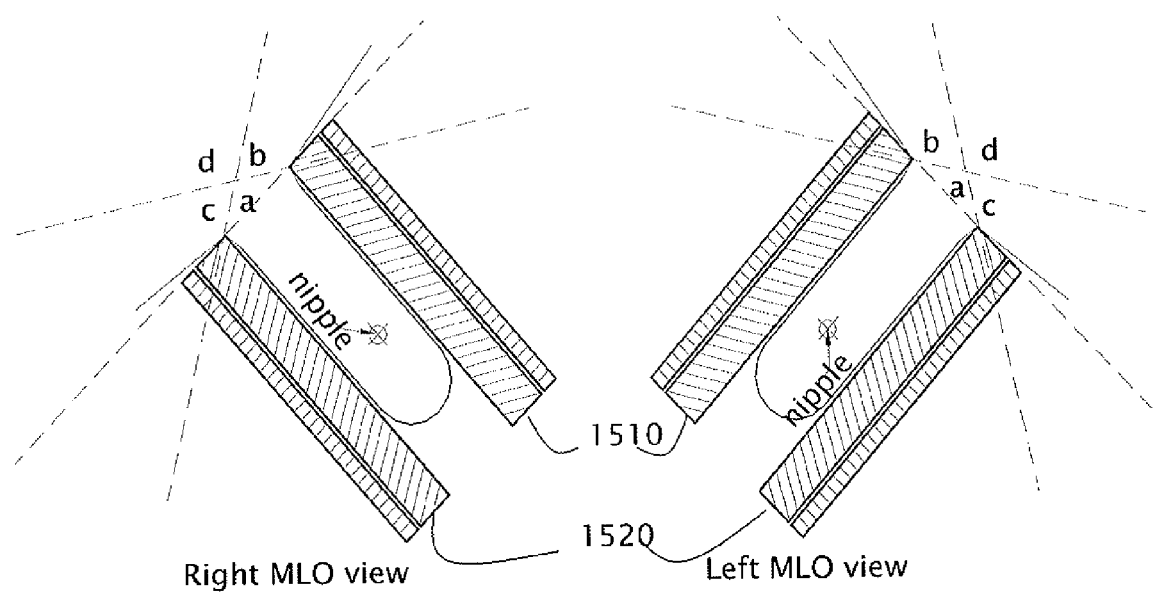
FIG. 15 illustrates a dual head molecular breast imaging arrangement with slanted collimators and its use for mammographic imaging.

For example FIGS. 15A and 15B illustrate respective right and left media-lateral oblique (MLO) breast views using the dual slanted collimators 1510 and 1520. The slanted collimators provide extended tissue coverage of breast tissue that is outside the active compression area of the detector heads. As labeled, region "a" has the full system sensitivity thereby enabling views of tissue within the chest wall. Regions "b" and "c" will have limited, but not zero, sensitivity, allowing partial sensitivity for tumor detection within the axilla tissue. Region "d" has no sensitivity for any tumor detection.

Figure 16:
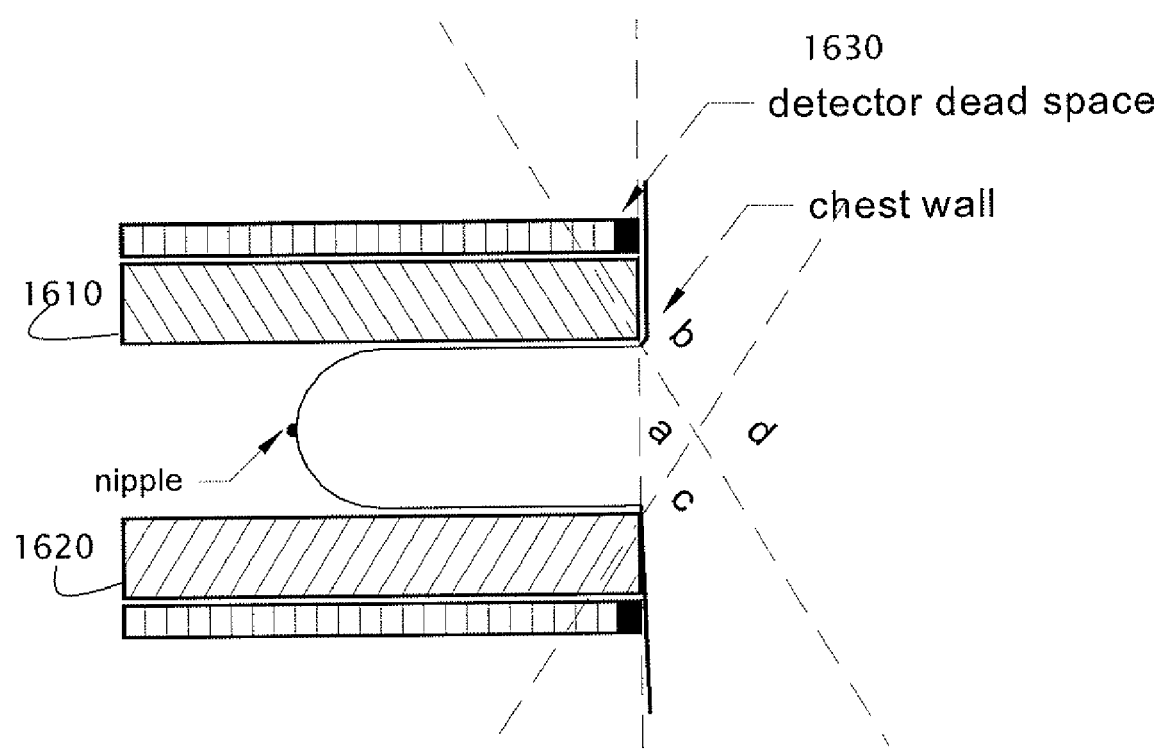
FIG. 16 is a side view of a dual head MBI system, provided to illustrate how the dual slanted collimator arrangement improves visualization of tissue in the chest wall.

FIG. 16 illustrates a side view of a CC breast compression. In general a detector edge has a finite thickness that limits the detection sensitivity of the breast tissue along an edge, referred to in FIG. 16 as the dead space 1630. The dead space can be as much as 5 to 7 mm. Any tumor that is within the dead space or further within the chest wall is not imaged with conventional x-ray imaging technology. However an gamma camera with a dual-slanged collimator overcomes the problems associated with detector dead space and even enables imaging of breast tissue "a" that extends into the chest wall. As in FIGS. 15A and 15B, use of the dual slanted collimators allows areas "b" and "c" to be imaged with some level of sensitivity.

Figure 17A:
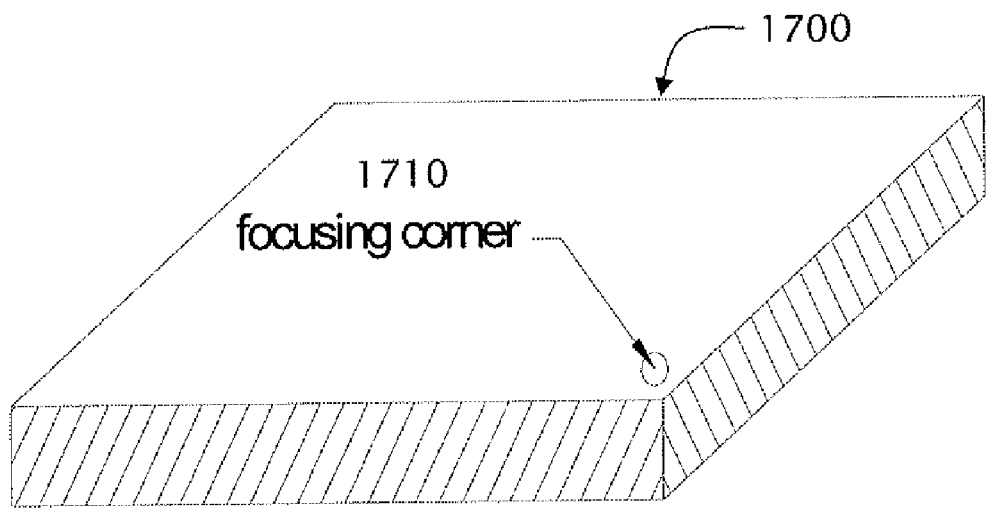
FIGS. 17A and 17B illustrate an alternative collimator design which may be used to improve sensitivity and tissue coverage for both the axilla and chest wall during MBI.
Figure 17B:
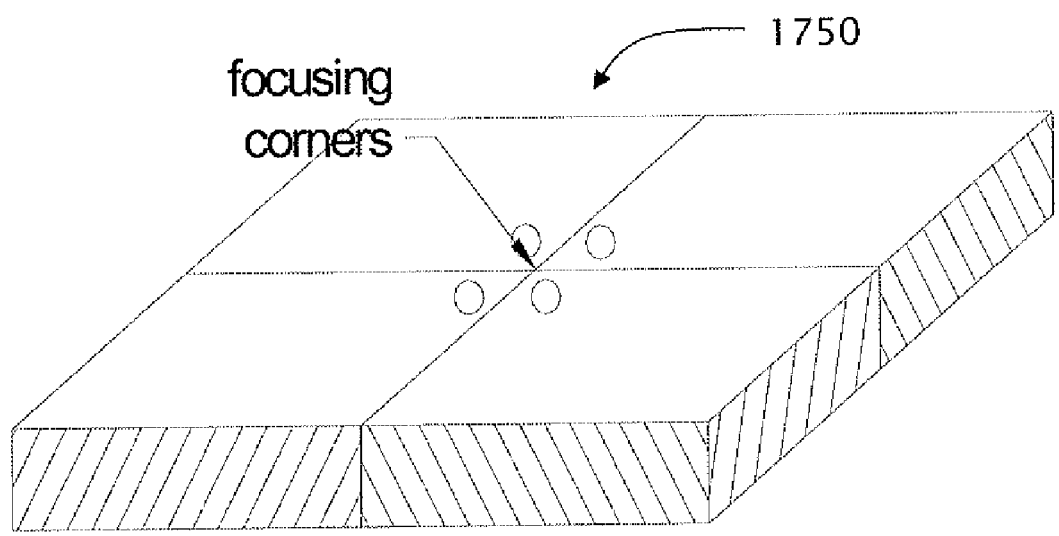

In order to improve tissue coverage of both axilla and the chest wall it is desirable to slant the collimator holes both in the lateral direction from left to right and in the nipple to the chest wall direction. FIGS. 17A and 17B illustrate respective examples 1700 and 1750 of such collimators. In FIG. 17A, one collimator 1700 that is designed to focus on a region of interest via the focusing corner 1710 is illustrated. FIG. 17B illustrates a second embodiment of a custom collimator that may be arranged to focus on a small region of interest with improved detection sensitivity. Each of the four collimator segments serves to image the lesion, and the sensitivity, or number of photons imaged in a given unit of time, is four times that of a single gamma camera with collimator pointing at the lesion.

To perform biopsies the dual-head MBI system the design should allow simultaneous, active tracing of needle location and easy access to the breast lesion. FIGS. 18A-18D illustrate various embodiments of a dual-head MBI system for needle biopsies. In FIG. 18A the cameras 1810 and 1820 are of similar size. Once the lesion is located, the needle 1830 (coated with tracer material) may be inserted into the breast. The slant collimators of camera 1810, in conjunction with data received from camera 1830, enables active tracing of the needle during the biopsy with real-time needle trajectory feedback. FIG. 18B illustrates an alternate embodiment, wherein once the lesion location is identified camera 1810 is replaced with a smaller camera assembly 1840, which is positioned such that the edge of camera 1840 clears the known location of the lesion to allow the biopsy needle to be directed at the lesion.

In the embodiment illustrated in FIGS. 18C and 18D, the top camera 1870 is comprised of two smaller detector/collimator assemblies 1870A and 1870B in close packaging to serve as a larger size imager. FIG. 18C illustrates the cameras 1870 and 1820 in an imaging position which is used for lesion localization. In one embodiment, once the lesion is detected and the location identified, one half of the assembly (1870B) may be removed to provide an arrangement such as that shown in FIG. 18B. According to another embodiment, once the lesion location is detected, the collimator from one half of the assembly (i.e., the collimator 1875 from portion 1870B) may be removed and flipped to provide a focusing collimator arrangement such as shown in FIG. 18D.

Thus it can be seen that the use of one or more slant collimators can greatly improve viewing coverage of a dual-head gamma camera breast imaging system, providing improved three-dimensional localization and biopsy capability as well as improved coverage of axilla and chest wall tissue. The dual-head gamma camera breast imaging capability may be provided in a dedicated system, or alternatively as part of the T/MBI imaging system described above with regard to FIGS. 1-13.

The above description thus details the use of a combination x-ray and gamma camera system for use in cancer screening, diagnosis and biopsy. It should further be appreciated that the system may be used to provide three dimensional coordinates of markers, for example such as the TriMark™ Marker provided by Suros System, Inc., a subsidiary of Hologic, Inc. In addition, the system may be used to dynamically track a radioactive needle during a biopsy, for example to perform image guided surgery.

Accordingly an integrated multi-modal breast imaging system and method of use has been shown and described. The system combines tomosynthesis imaging capability with molecular imaging capability in a single, integrated breast imaging device, resulting in a breast imaging system with increased sensitivity and sensitivity. Having described exemplary embodiments of the system, it should appreciated that the above specific examples and embodiments are illustrative, and many variations can be introduced on these examples and embodiments without departing from the spirit of the disclosure or from the scope of the appended claims. For example, elements and/or features of different illustrative embodiments may be combined with each other and/or substituted for each other within the scope of this disclosure and appended claims.

The invention claimed is:

1. A breast imaging device comprising:
    tomosynthesis imaging components for obtaining tomosynthesis images of an anatomical structure of a breast; and
    molecular imaging components for obtaining molecular breast images of a physiological structure of the breast, wherein the molecular imaging components comprise a first positionable gamma camera coupled to the gantry base and positioned above the breast during molecular image capture and a second positionable gamma camera selectively disposed within the receptor housing an positioned below the breast during molecular image capture, and each of the positionable gamma cameras removed from a field of view of the anatomical structure during tomosynthesis image capture.

2. The breast imaging device of claim 1 further comprising a compression assembly mounted on a gantry base and a receptor housing coupled to the gantry base.

3. The breast imaging system of claim 2 wherein the tomosynthesis imaging components comprise: an x-ray assembly pivotably mounted on the gantry base, the x-ray assembly comprising an x-ray source mounted on an x-support arm; and a digital detector disposed within the receptor housing.

4. The breast imaging system of claim 3 wherein a target of the x-ray source is selected from a group including tungsten and rhodium.

5. The breast imaging system of claim 2 wherein the receptor housing is sized to accommodate a digital detector, a gamma camera and an anti-scatter grid.

6. The breast imaging system of claim 2 wherein the compression assembly is used for both tomosynthesis imaging and molecular imaging, and wherein the compression assembly applies a different amount of compression for tomosynthesis imaging than for molecular imaging.

7. The breast imaging system of claim 1 wherein a positioning of the positionable gamma cameras is motor controlled.

8. The breast imaging system of claim 1 wherein a positioning of the positionable gamma cameras is manually controlled.

9. The breast imaging system of claim 1 wherein at least one of the positionable gamma cameras is at least one of retractable, rotatable and pivotable.

10. The breast imaging system of claim 1 wherein at least one of the positionable gamma cameras includes a removable collimator.

11. The breast imaging system of claim 10 wherein the removable collimator is at least one of retractable from the receptor housing, removable from the receptor housing or ejectable from the receptor housing.

12. The breast imaging system of claim 10 wherein movement of the collimator is motor controlled.

13. The breast imaging system of claim 10 wherein movement of the collimator is manually controlled.

14. The breast imaging system of claim 1 wherein the molecular imaging components comprise at least two collimators.

15. The breast imaging system of claim 1 wherein the molecular imaging components include a collimator with moveable collimation.

16. The breast imaging system of claim 1 wherein at least one of the positionable gamma cameras is a Positron Emission camera.

17. The breast imaging system of claim 1 wherein at least one of the positionable gamma cameras is a Single Photon Emission camera.

18. The breast imaging system of claim 1 further comprising a display for displaying the tomosynthesis images and the molecular breast images.

19. The breast imaging system of claim 18 wherein the tomosynthesis images comprise tomosynthesis projection images (Tp) and tomosynthesis reconstructed (Tr) images, and wherein the molecular breast images (MBI) comprise at least one of MBI projection images and MBI reconstructed images, and wherein the display is adapted to display any two of the Tr, Tp, MBI projection and MBI reconstructed images in any one of a cine mode, toggle mode, thumbnail mode or side by side mode.

20. The breast imaging system of claim 1 further comprising computer aided detection (CAD) tools for identifying potential lesions in any of the tomosynthesis and molecular breast images.

21. The breast imaging system of claim 1 wherein the tomosynthesis imaging component includes a digital detector, the molecular imaging components include a gamma detector and wherein the digital detector and gamma detector differ in size.

22. The breast imaging system of claim 21 wherein the molecular imaging components include a pair of gamma detectors, and wherein at least two of the tomosynthesis detector and pair of gamma detectors differ in size.

23. A method of imaging a breast in an integrated tomosynthesis/molecular breast imaging (T/MBI) device includes the steps of:
   immobilizing the breast;
   performing a tomosynthesis scan of the breast;
   positioning a first gamma camera to over the breast and a second gamma camera under the breast;
   obtaining a molecular image of the breast using the first and second gamma cameras ; and
   decompressing the breast.

24. The method of claim 23, further including the step of varying a compression of the breast between the step of performing the tomosynthesis scan and the step of obtaining the molecular image.

25. The method of claim 23 further including the step of removing molecular imaging components from an xray field of view prior to performing the tomosynthesis scan of the breast.

26. The method of claim 23 wherein the T/MBI device includes a gantry comprised of an x-ray assembly, a gantry base and a receptor housing and wherein the step of advancing a gamma camera proximate to the compressed breast includes the step of moving a gamma camera from within the gantry base into the receptor housing.

27. The method of claim 23 wherein the T/MBI device includes a gantry comprised of an x-ray assembly, a gantry base and a receptor housing, and wherein a compression assembly including a compression paddle having a compression well is slideably mounted to the gantry base, and wherein the step of advancing a gamma camera proximate to the compressed breast includes the step of moving a gamma camera from within the gantry base into the compression well of the compression paddle.

* * * * *